United States Patent
Choi et al.

(10) Patent No.: US 11,957,669 B2
(45) Date of Patent: Apr. 16, 2024

(54) PHARMACEUTICAL COMPOSITION CONTAINING (R)-N-[1-(3,5-DIFLUORO-4-METHANSULFONYLAMINO-PHENYL)-ETHYL]-3-(2-PROPYL-6-TRIFLUOROMETHYL-PYRIDIN-3-YL)-ACRYLAMIDE

(71) Applicant: AMOREPACIFIC CORPORATION, Seoul (KR)

(72) Inventors: Joon Ho Choi, Yongin-si (KR); Won Kyung Cho, Yongin-si (KR); Kwang-Hyun Shin, Yongin-si (KR); Byoung Young Woo, Yongin-si (KR); Ki-Wha Lee, Yongin-si (KR); Min-Soo Kim, Busan (KR); Jong Hwa Roh, Yongin-si (KR); Mi Young Park, Yongin-si (KR); Young-Ho Park, Yongin-si (KR); Eun Sil Park, Yongin-si (KR); Jae Hong Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 294 days.

(21) Appl. No.: 16/638,038

(22) PCT Filed: Aug. 10, 2018

(86) PCT No.: PCT/KR2018/009151
§ 371 (c)(1),
(2) Date: Feb. 10, 2020

(87) PCT Pub. No.: WO2019/031902
PCT Pub. Date: Feb. 14, 2019

(65) Prior Publication Data
US 2020/0215040 A1  Jul. 9, 2020

(30) Foreign Application Priority Data
Aug. 11, 2017 (KR) .................. 10-2017-0102316

(51) Int. Cl.
*A61K 31/44* (2006.01)
*A61K 9/00* (2006.01)
*A61K 47/38* (2006.01)

(52) U.S. Cl.
CPC ............ *A61K 31/44* (2013.01); *A61K 9/0014* (2013.01); *A61K 47/38* (2013.01)

(58) Field of Classification Search
CPC ....... A61K 31/44; A61K 9/0014; A61K 47/38
See application file for complete search history.

(56) References Cited

U.S. PATENT DOCUMENTS

| | | | |
|---|---|---|---|
| 2007/0104780 A1* | 5/2007 | Lipari | A61K 31/501 514/273 |
| 2008/0194638 A1 | 8/2008 | Dedhiya et al. | |
| 2008/0312234 A1* | 12/2008 | Kim | A61P 1/18 544/131 |
| 2009/0099189 A1 | 4/2009 | Ulven et al. | |
| 2010/0047297 A1 | 2/2010 | Petersen | |
| 2012/0295935 A1 | 11/2012 | Frid et al. | |
| 2013/0184290 A1 | 7/2013 | Padval et al. | |
| 2015/0004237 A1* | 1/2015 | Edgar | A61K 9/146 536/63 |

FOREIGN PATENT DOCUMENTS

| | | |
|---|---|---|
| EP | 1896016 B1 | 8/2010 |
| JP | 2008519817 A | 6/2008 |
| JP | 2017031065 A | 2/2017 |
| KR | 20020097298 A | 12/2002 |
| KR | 1020070045153 A | 5/2007 |
| KR | 1020160101554 A | 8/2016 |
| WO | 2001042222 A1 | 6/2001 |
| WO | 2002064543 A2 | 8/2002 |
| WO | 2006064283 A1 | 6/2006 |
| WO | 2008013414 A1 | 1/2008 |
| WO | 2008046788 A1 | 4/2008 |
| WO | 2008074413 A2 | 6/2008 |
| WO | 2011054436 A2 | 5/2011 |
| WO | 2012150952 A1 | 11/2012 |
| WO | 2014057003 A1 | 4/2014 |
| WO | 2014133196 A1 | 9/2014 |
| WO | 2015066584 A1 | 5/2015 |

OTHER PUBLICATIONS

ShinEtsu Cellulose Derivatives, Pharmacoat®, obtained on the web on Sep. 10, 2022. (Year: 2022).*
International Search Report and Written Opinion for International application No. PCT/KR2018/009151, dated May 7, 2019, 7 pages, ISA/KR.
Bin Tian et al., "A comparison of the effect of temperature and moisture on the solid dispersions: Aging and crystallization", International Journal of Pharmaceutics, 2014, pp. 385-392, vol. 475.
Lakshmi et al., "Formulation and Evaluation of Ibuprofen Topical Gel: a Novel Approach for Penetration Enhancement", International Journal of Applied Pharmaceuticals, 2011, pp. 25-30, vol. 3 issue 3.
Chang et al., "Mechanism of Sleep Disturbance in Children with Atopic Dermatitis and the Role of the Circadian Rhythm and Melatonin", International Journal of Molecular Sciences, Mar. 29, 2016, pp. 1-11, vol. 17:462.
Ciolacu et al., "Amorphous Cellulose—Structure and Characterization", Cellulose Chemistry and Technology, 2011, pp. 45, 13-21.

(Continued)

*Primary Examiner* — Genevieve S Alley
(74) *Attorney, Agent, or Firm* — LUCAS & MERCANTI, LLP

(57) ABSTRACT

One aspect of the present disclosure is a pharmaceutical composition which includes (R)—N-[1-(3,5-difluoro-4-methansulfonylamino-phenyl)-ethyl]-3-(2-propyl-6-trifluoromethyl-pyridin-3-yl)-acrylamide as a first component and a cellulosic polymer as a second component, wherein the composition of one aspect of the present disclosure has a formulation characteristic in which crystal formation is delayed for a long time.

16 Claims, 8 Drawing Sheets

(56) References Cited

OTHER PUBLICATIONS

Jun-Won Yun et al., "TRPV1 antagonist can suppress the atopic dermatitis-like symptoms by accelerating skin barrier recovery", Journal of Dermatological Science, 2010, pp. 8-15, vol. 62.

Kyung-Min Lim et al., Development of PAC-14028, a Novel Transient Receptor Potential Vanilloid Type 1 (TRPV1) Channel Antagonist as a New Drug for Refractory Skin Diseases, Archives of Pharmacal Research, 2012, pp. 393-396. vol. 35 No. 3.

Yang-Hui Park et al., "Oral and topical pharmacokinetic studies of a novel TRPV1 antagonist, PAC-14028 in rats and minipigs using liquid chromatography/tandem mass spectrometric method", 2011, pp. 8-14, vol. 61.

J-W Yun et al., "Antipruritic Effects of TRPV1 Antagonist in Murine Atopic Dermatitis and Itching Models", Journal of Investigative Dermatology, 2011, pp. 1576-1579, vol. 131.

Nian-qiu Shi, et al., "Rules and Characteristics of Crystallization Inhibition of Cellulose Polymers Against Drugs in Supersaturated States", Acta Pharmaceutica Sinica, vol. 51, No. 3, pp. 462-468, 2016.

Office Action for Corresponding Chinese Application No. 201880052207.X. and English Translation, dated Dec. 2, 2022, 12 Pages.

\* cited by examiner

[FIG. 1A]
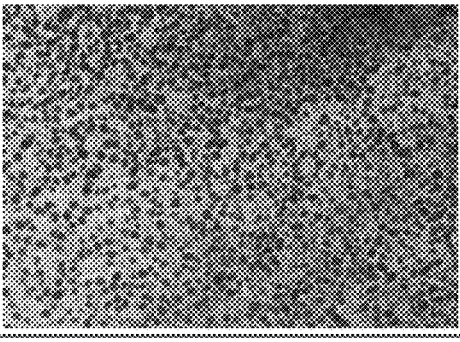

[FIG. 1B]
| | Optical image | Polarized image |
|---|---|---|
| Reference example 4 | 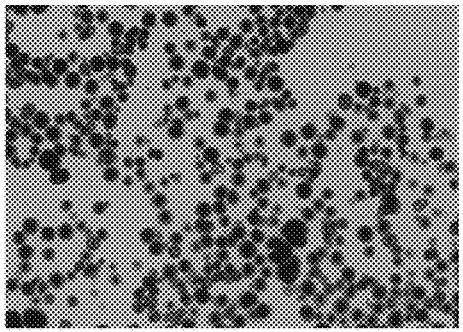 | 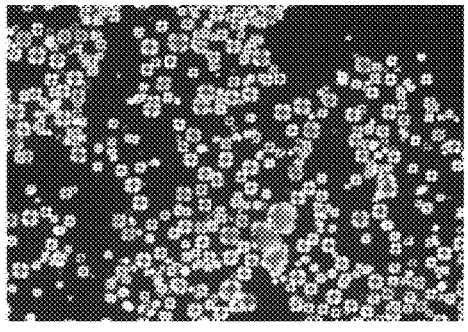 |
| Reference example 5 | 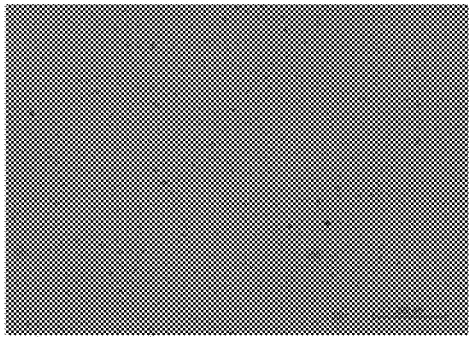 | 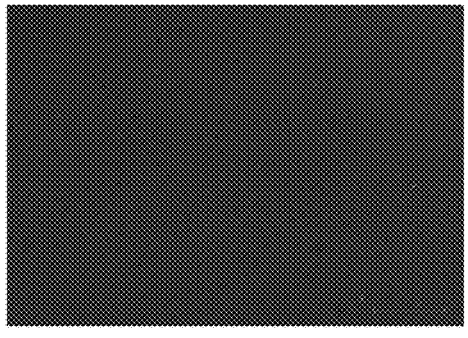 |
| Reference example 6 | 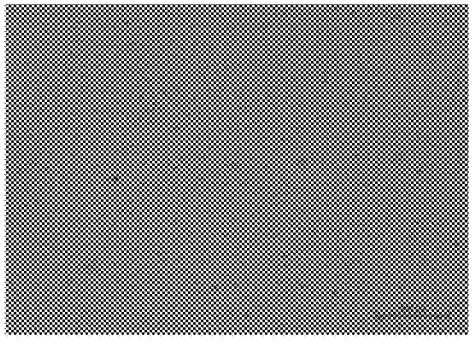 | 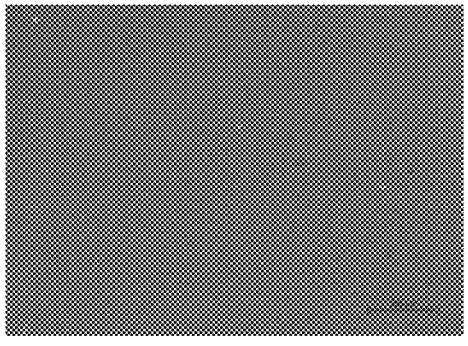 |

[FIG. 1C]
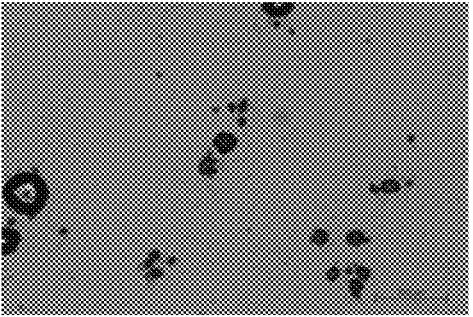

[FIG. 2A]

| | Optical image | Polarized image |
|---|---|---|
| Comparative example 1 | | |
| Comparative example 2 | | |
| Comparative example 3 | | |

[FIG. 2B]

| | Optical image | Polarized image |
|---|---|---|
| Example 1 | | |
| Example 2 | | |
| Example 3 | | |

[FIG. 2C]
| | Optical image | Polarized image |
|---|---|---|
| Example 4 | 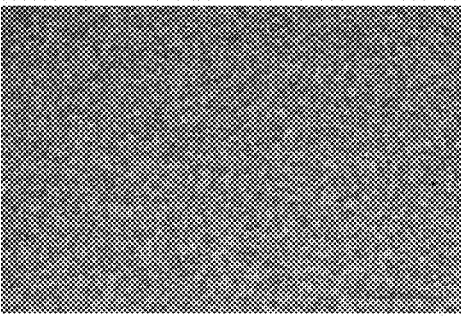 | 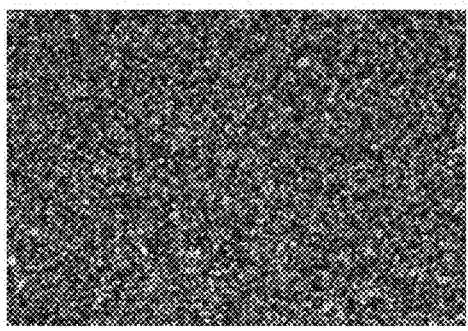 |
| Example 5 | 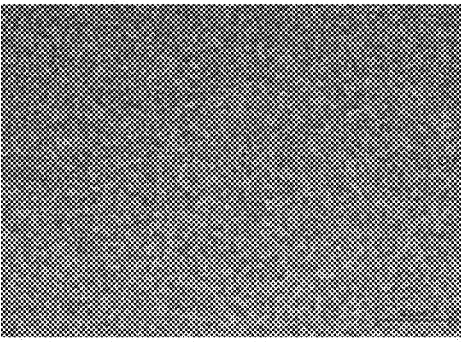 | 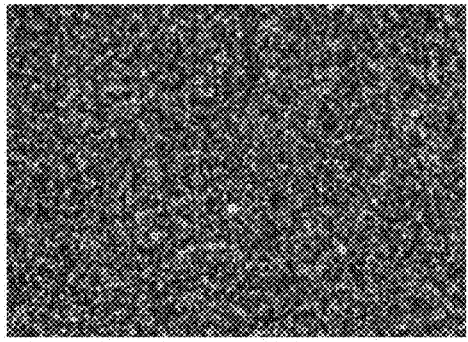 |
| Example 6 | 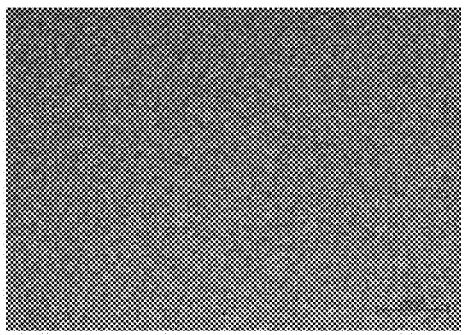 | 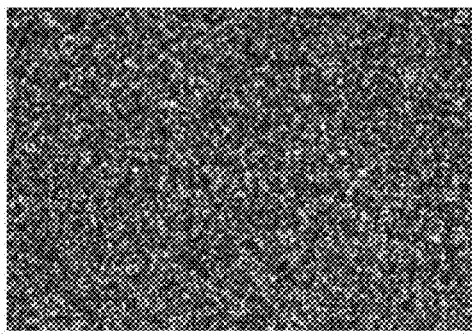 |

[FIG. 2D]
| | Optical image | Polarized image |
|---|---|---|
| Example 7 | 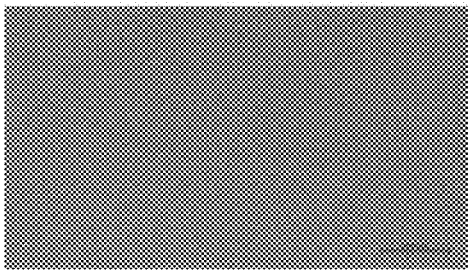 | 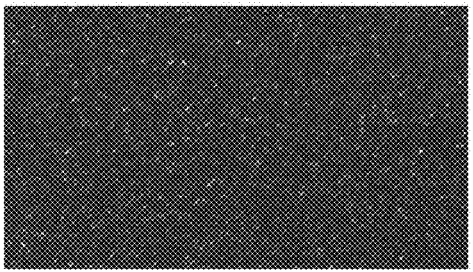 |
| Example 8 | 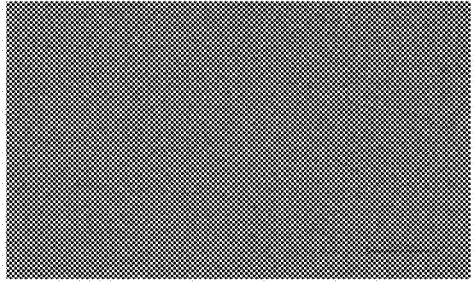 | 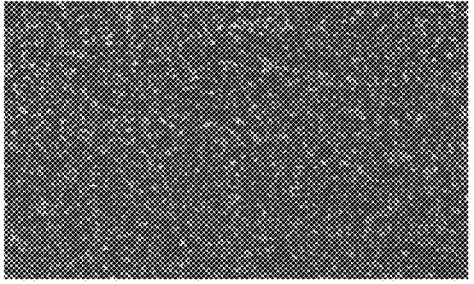 |
| Example 9 | 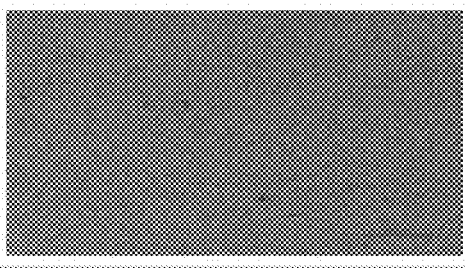 | 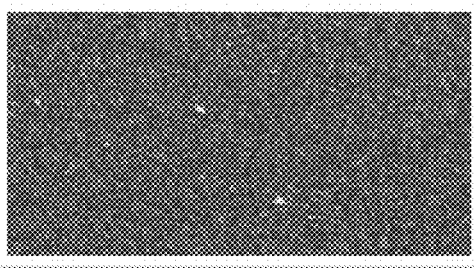 |
| Example 10 |  | 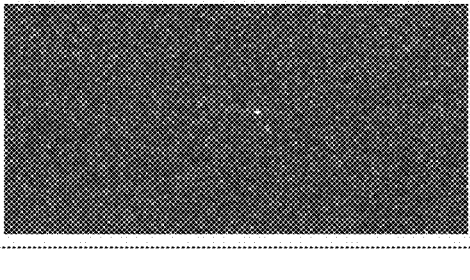 |

[FIG. 3]
| | Optical image | Polarized image |
|---|---|---|
| Example 8 (24months) | 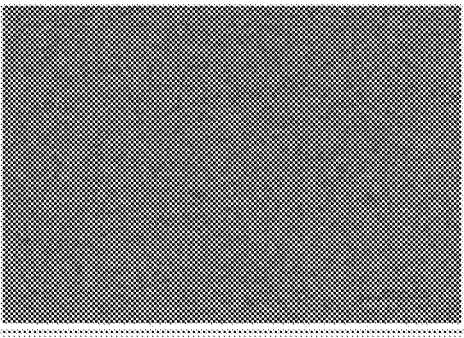 | 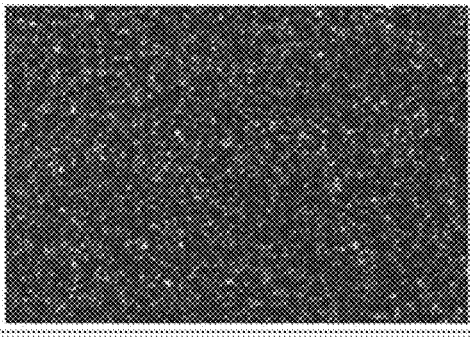 |
| Example 8 (31months) | 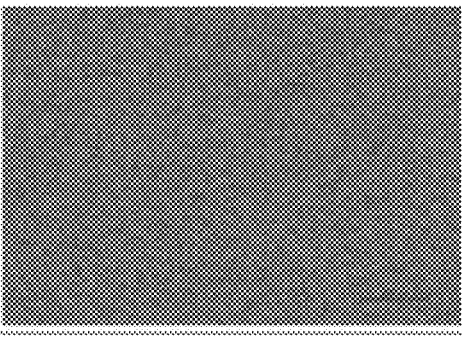 | 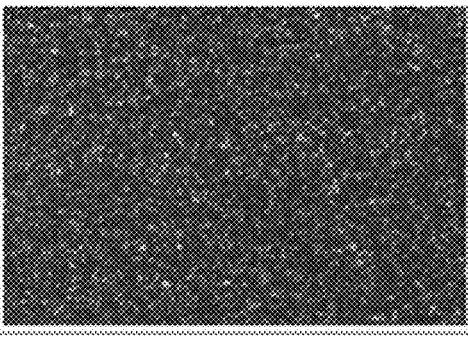 |

PHARMACEUTICAL COMPOSITION CONTAINING (R)-N-[1-(3,5-DIFLUORO-4-METHANSUL-FONYLAMINO-PHENYL)-ETHYL]-3-(2-PROPYL-6-TRIFLUOROMETHYL-PYRIDIN-3-YL)-ACRYLAMIDE

CROSS-REFERENCE TO RELATED APPLICATIONS

This application is a 371 U.S. national stage of PCT/KR2018/009151, filed Aug. 10, 2018 which claims the priority from Korean Patent Application No. 10-2017-0102316, filed Aug. 11, 2017, the contents of each of which are incorporated herein by reference.

TECHNICAL FIELD

The present invention relates to a pharmaceutical composition comprising (R)—N-[1-(3,5-difluoro-4-methanesulfonylamino-phenyl)-ethyl]-3-(2-propyl-6-trifluoromethyl-pyridin-3-yl)-acrylamide, which has an excellent feeling of use.

BACKGROUND ART

The compound (R)—N-[1-(3,5-difluoro-4-methanesulfonylamino-phenyl)-ethyl]-3-(2-propyl-6-trifluoromethyl-pyridin-3-yl)-acrylamide is represented by Formula (1)

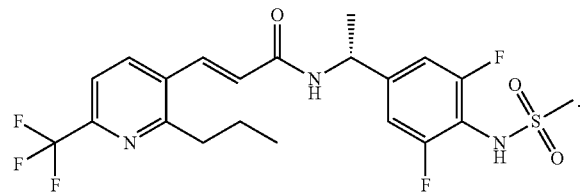 [SMILES: CCCc1nc(C(F)(F)F)ccc1/C=C/C(=O)N[C@H](C)c1cc(F)c(NS(C)(=O)=O)c(F)c1]

It is disclosed in Example 230 of WO 2008/013414.

The compound of Formula (1) has an antagonistic activity on the vanilloid receptor, and is a very useful compound that is expected to be used as an effective therapeutic agent for pain, neurological disorders, and dermatologic diseases such as atopic dermatitis, inflammatory diseases and the like. Particularly, in the case of muscle pain or dermatologic diseases, it may be desirable to topically apply directly to the skin. Therefore, as one of the formulations suitable for the compound of Formula (1), a pharmaceutical composition for an external use is required.

It has been found that the compound of Formula (1) has a solubility in water of less than 0.1 mg/mL and thus is poorly soluble. In order to formulate a drug which is poorly soluble in water into a pharmaceutical composition for an external use, water is generally not used or its content is minimized, and a solvent that can solubilize a poorly soluble substance is used. However, such a solvent may adversely affect the skin or can make the feeling of use worse. Particularly, when such a solvent is applied to a patient having the increased sensitivity such as atopic dermatitis, the atopic dermatitis may be worse or the medication compliance may be reduced, thereby eventually affecting treatment. It was also found that the compound of Formula (1) is not only poorly soluble in water but also has a significantly low solubility in oil.

In order to improve the poor solubility in water, an attempt has been made to make the poorly soluble substance into the amorphous state using a polymer and then to prepare a pharmaceutical composition for an external use. However, the amorphous state is basically unstable and particularly vulnerable to temperature and humidity (International Journal of Pharmaceutics 475 (2014) 385-392), and since the pharmaceutical composition for an external use usually already includes water, it is difficult to inhibit crystallization from the amorphous state by a conventional method.

Another method related to the pharmaceutical composition for an external use containing the poorly soluble substance is to mix a separately prepared solid dispersion with the solvent selected for the pharmaceutical composition for an external use. However, such method fails to provide specific data to inhibit crystallization to the extent that it is possible to ensure the shelf life of drug product for the pharmaceutical composition for an external use as a complete product (J. DRUG DEL. SCI. TECH., 21 (6) 509-516 2011, Int. J App Pharm.).

As such, it is necessary to develop a pharmaceutical composition which contains the compound of formula (1) which has poor solubility in water and in oil which makes it difficult to formulate, and which has an excellent feeling of use, and which substantially inhibits the formation of crystals for at least two years.

DISCLOSURE

Technical Problem

The inventors of the present invention have confirmed that by using a cellulosic polymer, a pharmaceutical composition containing the compound of Formula (1) demonstrates delayed the formation of crystals over a long period of time and has an excellent feeling of use.

Therefore, it is an object of the present invention to provide a pharmaceutical composition having an excellent feeling of use substantially without the formation of crystals, which comprises the compound (R)—N-[1-(3,5-difluoro-4-methanesulfonylamino-phenyl)-ethyl]-3-(2-propyl-6-trifluoromethyl-pyridin-3-yl)-acrylamide represented by formula (1) as a first component and a cellulosic polymer as a second component.

Technical Solution

In order to achieve the above object, the present invention provides a pharmaceutical composition comprising the compound of (R)—N-[1-(3,5-difluoro-4-methanesulfonylamino-phenyl)-ethyl]-3-(2-propyl-6-trifluoromethyl-pyridin-3-yl)-acrylamide represented by the following Formula (1) as a first component and a cellulosic polymer as a second component.

In addition, the present invention provides a method of inhibiting the formation of crystals from the pharmaceutical composition comprising the compound of (R)—N-[1-(3,5-difluoro-4-methanesulfonylamino-phenyl)-ethyl]-3-(2-propyl-6-trifluoromethyl-pyridin-3-yl)-acrylamide represented by formula (1) as a first component, which comprises adding the cellulosic polymer as a second component.

Advantageous Effects

The pharmaceutical composition of the present invention inhibits the crystallization of the active component of the compound of Formula (1).

BRIEF DESCRIPTION OF THE DRAWINGS

FIGS. 1A to 1C are images obtained by an optical and polarization microscope observing the presence or absence of crystal precipitation after storing the compositions 1 to 8 of Reference examples in a chamber at 40° C. for 24 hours, respectively.

FIGS. 2A to 2D are images obtained by an optical and polarization microscope observing the presence or absence of crystal precipitation after storing the compositions 1 to 3 according to Comparative examples and the compositions 1 to 10 according to Examples of the embodiment of the invention in a constant temperature chamber at 40° C., which is an acceleration condition, for 2 weeks, respectively.

FIG. 3 is an image obtained by an optical and polarization microscope observing the presence or absence of crystal precipitation after the composition 8 of Example of the embodiment of the invention for 24 months and 31 months under a long-term storage condition.

DETAILED DESCRIPTION OF THE INVENTION

The present invention provides a pharmaceutical composition which substantially inhibits the formation of crystals for extended periods of time by inducing a specific polymer therein.

The pharmaceutical composition according to the present invention comprises the compound represented by Formula (1)

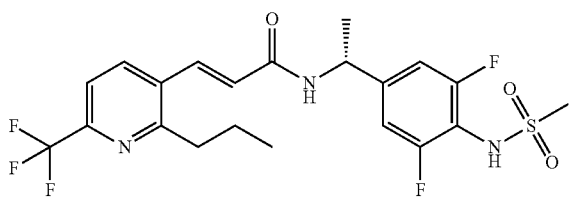 [SMILES: CCCc1nc(C(F)(F)F)ccc1/C=C/C(=O)N[C@H](C)c1cc(F)c(NS(C)(=O)=O)c(F)c1]

as a first component and the cellulosic polymer as a second component.

The compound represented by formula (1) is the antagonist of vanilloid receptor-1 (VR1, or TRPV1 (transient receptor potential vanilloid-1)), and is useful for pain, neurological disorders, dermatologic diseases such as atopic dermatitis, inflammatory diseases and the like. The compound of Formula (1), its preparation method and its antagonistic activity on the vanilloid receptor are described in detail in PCT International Patent Publication No. WO 2008/013414, the contents of which are incorporated herein by reference.

In the present invention, the compound of Formula (1) includes both pharmacologically acceptable salts as well as the parent compound. Examples include (1) an acid addition salt formed from an inorganic acid or formed from an organic acid; or (2) salts formed when the acidic proton present in the parent compound is substituted.

The compound of Formula (1), which is the first component of the pharmaceutical composition, may be included in an amount of about 0.1 to 1.5 wt. %, preferably about 0.5 to 1.2 wt. %, more preferably about 0.8 to 1.2 wt. %, based on the total weight of the composition. If the content of the compound represented by formula (1) is less than about 0.1 wt. %, the desired therapeutic effect may not be exhibited. If the content exceeds about 1.5 wt. %, the content of the solvent and the second component is relatively reduced, and thus the feeling of use and the inhibitory crystal formation effect may be reduced.

In the present invention, the cellulosic polymer used in the present invention substantially inhibits the formation of crystals of the compound of Formula (1), in the pharmaceutical compositions of the present invention, for extended periods, i.e. 3 years, of time and promotes the feeling of use. Suitable cellulosic polymers are readily available and have the characteristic of easy structural modification through a chemical reaction, and are generally used extensively as an excipient in pharmaceutical compositions. However, in the present invention, the cellulosic polymers inhibit the formation of crystals of the compound of Formula (1).

The cellulosic polymers used in the present invention can be selected from the group among methyl cellulose, hydroxyethylcellulose, hydroxypropylcellulose and hypromellose, and may be further selected from among hydroxyethylcellulose, hydroxypropylcellulose and hypromellose. Hypromellose is more preferred.

The content of the cellulosic polymer may be about 1 to 5 wt. %, preferably about 1 to 3 wt. %, more preferably about 2.5 wt. % of the total weight of the pharmaceutical composition of the present invention. If the content of the cellulosic polymer is less than about 1 wt. %, the inhibitory effect on the formation of crystals is insignificant and thus crystals are precipitated from the pharmaceutical composition. If the content of the cellulosic polymer is more than about 5 wt. %, the crystals will not be precipitated but the feeling of use may be reduced.

In addition, the cellulosic polymer may have a weight ratio of about 1 to 3:1, preferably about 1.5 to 3:1, more preferably about 2 to 3:1 relative to the compound represented by formula (1). If the weight ratio is less than the above range, the inhibitory effect on the formation of crystals is insignificant and thus crystals may be precipitated from the pharmaceutical composition. If the weight ratio exceeds the above range, the crystals will not be precipitated but the feeling of use may be reduced.

In addition, the viscosity of the cellulosic polymer may be about 2 to 20 mPa·s, preferably about 2 to 16 mPa·s, more preferably about 2 to 10 mPa·s, and most preferably about 2 to 6 mPa·s. At this time, the viscosity is a viscosity of a 2% (w/v) aqueous solution at 20° C. If the viscosity is less than about 2 mPa·s, the inhibitory effect on the formation of crystals is insignificant and thus crystals may be precipitated from the pharmaceutical composition. If the viscosity is more than about 20 mPa·s, the feeling of use may not be good, especially when applied to patients having increased sensitivity due to conditions such as atopic dermatitis. The atopic dermatitis may become worse or the medication compliance may be reduced, thereby eventually affecting the treatment effect.

Specifically, among these cellulosic polymers, the hydroxypropylcellulose is hydroxypropylcellulose LF which has a viscosity of about 6.0-10.0 mPa·s in a 2% (w/v) aqueous solution at 20° C., or hydroxypropylcellulose EF which has a viscosity of about 150-400 mPa·s. Hydroxypropylcellulose LF is preferred in these aspects of the invention.

The cellulosic polymer inhibits the formation of crystals of the compound of Formula (1) to such an extent that when observed at a magnification of 100 or more, specifically, at a magnification of 100, preferably at a magnification of 500, more preferably at a magnification of 1000 by a microscope (for example, BX50 of Olympus), crystals are not observed. With respect to the presence or absence of crystal precipitation at this time, when dark brown irregular particles are observed in the optical image and anisotropic particles are observed in the polarized image at the same position at the same time, it is judged that there is a crystal precipitation.

The solvent used in the present invention can be used to dissolve the compound of Formula (1) which is poorly soluble. Solvents, which ensure a high solubility of the compound of Formula (1) and thus are capable of dissolving it even in a small amount and which have a high safety, are suitable.

The solvents used in the present invention will ensure solubility of the compound of Formula (1) of 100 mg/mL or more, preferably 120 mg/mL or more, more preferably 150 mg/mL or more.

The solvent may be at least one selected from among diethylene glycol monoethyl ether, polyethylene glycol, 2-pyrrolidone, and dimethyl sulfoxide. Preferably the solvent is diethylene glycol monoethyl ether and polyethylene glycol, or more preferably may be polyethylene glycol. The polyethylene glycol may be polyethylene glycol 300 or polyethylene glycol 400, which is preferred.

The solvent may be included in an amount of about 5 to 20 wt. %, preferably about 5 to 15 wt. %, more preferably about 8 to 12 wt. % of the total weight of the composition. If the content of the solvent is less than about 5 wt. %, the compound represented by formula (1) cannot be completely dissolved. If the content is more than about 20 wt. %, the solvent may be too much and thus the feeling of use may be reduced.

The pharmaceutical composition of the present invention can be formulated into a pharmaceutical composition for an external, especially atopical, use and thus formulated into a cream, gel, patch, aerosol, ointment, plaster, lotion, liniment, cataplasma, essence, pack, powder, oil, wax, spray, paste, solution, suspension, emulsion or soap formulation, for example.

Meanwhile, the formulation may further comprise known components commonly used in the art depending on the desired formulation so long as they do not impair the effect of the compound of Formula (1). According to one embodiment, the formulation may further comprise additives such as carriers, emulsifiers, moisturizers, skin conditioning agents, surfactants, chelating agents, antioxidants, bactericides, stabilizers, and any combination thereof.

The carriers may include, but are not limited to, animal fibers, vegetable fibers, wax, paraffin, starches, tragacanth, cellulose derivatives, polyethylene glycol, silicone, bentonite, silica, talc, zinc oxide, lactose, aluminum hydroxide, calcium silicate, polyamide powder, water, ethanol, isopropanol, ethyl carbonate, ethyl acetate, benzyl alcohol, benzyl benzoate, propylene glycol, 1,3 butylene glycol, glycerol aliphatic esters, polyethylene glycol, liquid diluents, ethoxylated isostearyl alcohol, suspending agents such as polyoxyethylene sorbitol ester and polyoxyethylene sorbitan ester, microcrystalline celluloses, aluminum metahydroxide, agar, aliphatic alcohol sulfates, aliphatic alcohol ether sulfates, sulfosuccinic acid monoester, isethionate, imidazolinium derivatives, methyl taurate, sarcosinate, fatty acid amide ether sulfates, alkylamido betaine, aliphatic alcohols, fatty acid glyceride, fatty acid diethanol amide, vegetable oils, linolenic derivatives, ethoxylated glycerol fatty acid ester or the like.

The moisturizers may include, but are not limited to, glycerine, glyceryl stearate, and the like.

The skin conditioning agents may include, but are not limited to, cyclomethicone, dimethicone, and the like.

The surfactants may include, but are not limited to, polyoxyethylene sorbitan-fatty acid esters, polyoxyethylene fatty acid esters, sorbitan fatty acid esters, polyoxyethylene-polyoxypropylene copolymer, cetearyl glucoside, mono/diglycerides and the like.

The chelating agents may include, but are not limited to, sodium ethylenediaminetetraacetate (EDTA), α-hydroxy fatty acid, lactoferrin, α-hydroxy acid, citric acid, lactic acid, malic acid, bilirubin, biliverdin and the like.

The antioxidants may include, but are not limited to, butylhydroxyanisole, dibutylhydroxytoluene, propyl gallate, and the like.

In addition components that can be incorporated into the pharmaceutical composition include pH adjusters, plasticizers, solubilizing agents, gelling agents, binders, isotonic agents, analgesics, preservatives, dispersants, opacifiers, antioxidants, osmolality adjusting agents, defoaming agents, wetting agents, thickening agents, tackifiers, shielding agents, coloring agents, flavoring agents, film forming agents, suspending agents, volatile restrainers, adsorbents, oily components, emollients, organic and inorganic pigments, organic powders, ultraviolet absorbers, alcohols, blood circulation accelerators, cool feeling agents, antiperspirants and the like.

The preferred single dose of the pharmaceutical composition of the present invention depends on the condition, the weight and the severity of disease of the patient, the form of the composition, and routes and duration of administration. However, in the case of the application of pharmaceutical composition for an external use to be applied atopically, the dose (1 finger-tip unit (FTU), 0.5 g), as obtained when squeezing a cream as long as one straight line from the tip of the index finger of the patient to the first distal interphalangeal joint, corresponds to an dose for one application which is suitable for applying 2 times the area (~2% BSA) of the patient's palm size.

At this time, BSA (Body Surface Area) refers to the area of the lesion site, and is a value obtained by evaluating the area of the lesion site relative to 100% of the entire skin area according to Rule of 9.

Specifically, when the subject to which the pharmaceutical composition one aspect of the present disclosure is to be administered is a patient suffering from atopic dermatitis, for example, a patient having a 5% to 30% BSA lesion, the single dose may preferably be 25 mg to 150 mg, and the dosage can be appropriately regulated within the range of the single dose in consideration of the size, shape and severity of the lesion, and the age of the patient.

As described above, since the pharmaceutical composition of the present invention contains the compound of Formula (1), which is the antagonist of TRPV1, as an effective component, the composition may be used for therapeutic purposes for diseases that can be treated by the antagonistic effect of TRPV1, such as pain, dermatologic diseases such as atopic dermatitis and the like. In addition, since the feeling of use is also enhanced, the composition may be formulated to be particularly suitable for a pharmaceutical composition for an external use on the skin.

The pharmaceutical composition of the present invention may preferably be in the form of an oil-in-water (O/W) emulsion comprising, (1) the compound of Formula (1) as a drug which is the first component;

(2) the cellulosic polymer as a second component;

(3) at least one component selected from the group consisting of diethylene glycol monoethyl ether, polyethylene glycol, 2-pyrrolidone and dimethyl sulfoxide as the solvent;

(4) water as an aqueous phase component;

(5) at least one component selected from the group consisting of PEG-30 hydrogenated castor oil, medium chain triglyceride, cetostearyl alcohol, squalane and cyclomethicone as an oil phase component;

(6) at least one component selected from the group consisting of polyoxyethylene-sorbitan-fatty acid esters, polyoxyethylene fatty acid esters, sorbitan fatty acid esters, polyoxyethylene-polyoxypropylene copolymer, cetearyl glucoside and mono/diglycerides as a surfactant; and (7) at least one component selected from the group consisting of xanthan gum, gelatin, gellan gum, carrageenan and carbomer as a thickening agent.

The content of the compound of Formula 1, in the composition of the present invention, may be about 0.1 to 1.5 wt. % of the total weight of the composition. The content of the cellulosic polymer which is the second component may be about 1 to 5 wt. % of the total weight of the composition. The content of the solvent may be about 5 to 20 wt. % of the total weight of the composition. The content of the aqueous phase may be about 45 to 90 wt. % off the total weight of the composition. The content of the oily phase may be about 5 to 30 wt. %. The content of the surfactant may be about 1 to 10 wt. %. The content of the thickening agent may be about 0.01 to 5 wt. %.

In addition, the present invention provides a method for substantially inhibiting the formation of crystals from the pharmaceutical composition comprising the compound of (R)—N-[1-(3,5-difluoro-4-methanesulfonylamino-phenyl)-ethyl]-3-(2-propyl-6-trifluoromethyl-pyridin-3-yl)-acrylamide represented by Formula (1) as a first component, which comprises adding the cellulosic polymer as a second component.

Examples

Item 1. A pharmaceutical composition comprising the compound of (R)—N-[1-(3,5-difluoro-4-methanesulfonylamino-phenyl)-ethyl]-3-(2-propyl-6-trifluoromethyl-pyridin-3-yl)-acrylamide represented by the following Formula (1) and a cellulosic polymer:

Formula (1)

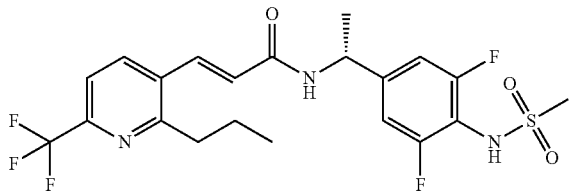 [SMILES: CCCc1nc(C(F)(F)F)ccc1/C=C/C(=O)N[C@H](C)c1cc(F)c(NS(C)(=O)=O)c(F)c1]

Item 2. The pharmaceutical composition according to item 1, wherein the cellulosic polymer inhibits the formation of crystals of the compound of Formula (1).

Item 3. The pharmaceutical composition according to item 1 or 2, wherein when observed at a magnification of 100 or more, preferably at a magnification of 500 or more, more preferably at a magnification of 1000 or more using an optical microscope, the crystals of compound of Formula (1) are not observed in the pharmaceutical composition.

Item 4. The pharmaceutical composition according to item 3, wherein the optical microscope is equipped with a polarizing filter.

Item 5. The pharmaceutical composition according to any one of items 1 to 4, wherein the cellulosic polymer has at least one of the following characteristics (i) to (iii):

(i) a viscosity of 2 to 20 mPa·s, preferably 2 to 16 mPa·s, more preferably 2 to 10 mPa·s, most preferably 2 to 6 mPa·s, (ii) a content of 1 to 5 wt. %, preferably 1 to 3 wt. %, more preferably 2.5 wt. % of the total weight of the composition, or (iii) a weight ratio of 1 to 3:1, preferably 1.5 to 3:1, more preferably 2 to 3:1 relative to the compound represented by Formula (1).

Item 6. The pharmaceutical composition according to any one of items 1 to 5, wherein the cellulosic polymer may be at least one selected from the group consisting of methyl cellulose, hydroxyethylcellulose, hydroxypropylcellulose and hypromellose, or preferably at least one selected from the group consisting of hydroxyethylcellulose, hydroxypropylcellulose and hypromellose, or more preferably hypromellose.

Item 7. The pharmaceutical composition according to any one of items 1 to 6, wherein the composition further comprises a solvent which ensures that the solubility of the compound of Formula (1) in the solvent is 100 mg/mL or more, preferably 120 mg/mL or more, more preferably 150 mg/mL or more.

Item 8. The pharmaceutical composition according to item 7, wherein the solvent is at least one selected from the group consisting of diethylene glycol monoethyl ether, polyethylene glycol, 2-pyrrolidone and dimethyl sulfoxide, or preferably at least one selected from the group consisting of diethylene glycol monoethyl ether and polyethylene glycol, or more preferably polyethylene glycol.

Item 9. The pharmaceutical composition according to item 7, wherein the polyethylene glycol is polyethylene glycol 300 or polyethylene glycol 400, preferably polyethylene glycol 400.

Item 10. The pharmaceutical composition according to any one of items 7 to 9, wherein the solvent is included in an amount of 5 to 20 wt. %, preferably 5 to 15 wt. %, more preferably 8 to 12 wt. %, most preferably 10 wt. % of the total weight of the composition.

Item 11. The pharmaceutical composition according to any one of items 1 to 10, wherein the compound represented by formula (1) is included in an amount of 0.1 to 1.5 wt. %, preferably 0.5 to 1.2 wt. %, more preferably 0.8 to 1.2 wt. %.

Item 12. The pharmaceutical composition according to any one of items 1 to 11, wherein the pharmaceutical composition is formulated into a pharmaceutical composition for an external use which is applied to the skin.

Item 13. The pharmaceutical composition according to any one of items 1 to 12, wherein the pharmaceutical composition is formulated into a cream, gel, patch, aerosol, ointment, plaster, lotion, liniment, pasta or cataplasma formulation.

Item 14. A method of inhibiting the formation of crystals of the compound of Formula (1) from the pharmaceutical composition comprising the compound of (R)—N-[1-(3,5-difluoro-4-methanesulfonylamino-phenyl)-ethyl]-3-(2-propyl-6-trifluoromethyl-pyridin-3-yl)-acrylamide represented by formula (1), which comprises adding hypromellose:

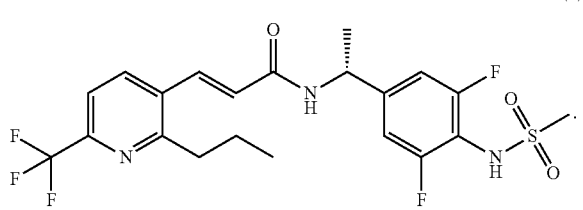

Formula (1)

In the following Experimental Examples, the compound of Formula (1) refers to (R)—N-[1-(3,5-difluoro-4-methanesulfonylamino-phenyl)-ethyl]-3-(2-propyl-6-trifluoromethyl-pyridin-3-yl)-acrylamide.

Preliminary Experiment Example 1: Selection of solvent suitable for compound of Formula (1)

In order to select a solvent capable of solubilizing the compound of Formula (1) that is poorly soluble in water as well as in oil, a solubility experiment for the compound of Formula (1) were conducted in the various solvents listed in Table 1 below. Since a small amount of solvent that ensures a high solubility can dissolve the compound of Formula (1) compared to a solvent that ensures a low solubility, the solvent that ensures the high solubility can contain the relatively higher content of water, especially when formulated into a pharmaceutical composition for an external use, thereby further enhancing the feeling of use.

An excess amount of the compound of Formula (1) was added to 1 mL of each solvent described in Table 1 below and stirred for 24 hours at 25° C. while shaking at 200 rpm (Shaking incubator, SI 600R, JEIO TECH, Korea). Thereafter, a centrifugation was performed at 10,000 rpm for 10 minutes, and the supernatant was filtered using a membrane filter (0.2 μm), then diluted moderately with methanol and analyzed by HPLC. The solubility of the compound of Formula (1) in each solvent was calculated from the results of analysis, and the results are shown in Table 1 below.

TABLE 1

| Chemical name | Solubility(mg/mL) |
|---|---|
| Purified water | 0.05 |
| Diethylene glycol monoethyl ether | 288.92 |
| Acetonitrile | 108.06 |
| Methanol | 177.68 |
| Ethanol | 75.32 |
| Dimethyl sulfoxide | 631.85 |
| Polyethylene glycol(PEG) 400 | 167.73 |
| Miglyol | 1.40 |
| Ethyl oleate | 1.00 |
| Corn oil | 1.80 |
| Dimethylacetamide | 80.00 |
| Propylene glycol | 25.00 |
| Polysorbate 80 | 11.80 |
| Caprylocaproyl polyoxyl-8 glycerides | 46.70 |
| Lauroyl macrogol-32 glycerides | 24.10 |
| Polyethylene glycol-35 castor oil | 2.70 |
| 2-Pyrrolidinone | 212.00 |
| Polyoxyl 40 hydrogenated castor oil | 36.00 |
| Polysorbate 20 | 47.97 |
| Polysorbate 60 | 35.04 |
| Polysorbate 40 | 37.02 |
| Propylene glycol monocaprylate | 75.00 |
| Octyldodecanol | 1.77 |
| Oleyl Alcohol | 6.32 |
| Isopropyl myristate | 1.18 |
| Oleic acid | 0.43 |
| Cocoyl caprylocaprate | 0.46 |
| Propylene glycol monolaurate | 7.75 |
| Oleoyl polyoxyl-6 glycerides | 4.36 |

TABLE 1-continued

| Chemical name | Solubility(mg/mL) |
|---|---|
| Glycerol | 0.84 |
| Polyethylene glycol(PEG) 300 | 145.73 |
| Poloxamer 124 | 66.69 |
| Triglycerides, Medium chain | 1.9 |
| Triacetin | 56.53 |

As can be seen from Table 1 above, the compound of Formula (1) has the high solubility of 100 mg/ml or more in relation to dimethyl sulfoxide (DMSO, Sigma-Aldrich), diethylene glycol monoethyl ether (Sigma-Aldrich), 2-pyrrolidone (Aldrich), and polyethylene glycol (PEG, Sanyo) and thus they can be used as a solvent suitable for the compound of Formula (1). However, it is difficult to formulate simply by using only these solvents because the solubility of the compound of Formula (1) is significantly lower in a composition having a high content of the aqueous phase. For example, the solubility in a 10% (w/w) aqueous solution of PEG 400 is about 0.08 mg/mL, which is practically insoluble.

Preparation Example 1: Preparation of Composition of Reference Example of the Present Invention 1) Preparation of Cellulosic Polymer Eight kinds of cellulosic polymers, i.e., methyl cellulose (MC, Metolose, Shinetsu), hydroxyethylcellulose (HEC, Natrosol, Ashland), hydroxypropylcellulose (HPC, Klucel, Ashland) LF and EF grades, and 3, 4.5, 6, and 15 mPas types of hypromellose (Hypromellose, Shinetsu) 2910 having properties as shown in Table 2 below were prepared.

TABLE 2

| | Cellulosic polymer | Vis. (mPa · s) |
|---|---|---|
| Reference Example 1 | MC | 12.0-18.0 |
| Reference Example 2 | HEC | 7.1-13.3 |
| Reference Example 3 | HPC LF | 6.0-10.0 |
| Reference Example 4 | HPC EF | 150-400 |
| Reference Example 5 | Hypromellose 3 | 2.4-3.6 |
| Reference Example 6 | Hypromellose 4.5 | 4.0-6.0 |
| Reference Example 7 | Hypromellose 6 | 4.8-7.2 |
| Reference Example 8 | Hypromellose 15 | 12.0-18.0 |

2) Preparation of Compositions 1 to 8 of Reference Examples of the Pharmaceutical Composition of the Present Invention The first solution was prepared by dissolving 1 g of the compound of Formula (1) in 10 g of PEG 400, one of the solvents identified from Preliminary Experimental Example 1 to be suitable. 2 g each of methyl cellulose (MC), hydroxyethylcellulose (HEC), hydroxypropylcellulose (HPC) LF and EF grades, and 3, 4.5, 6 and 15 mPas types of hypromellose 2910 polymers as shown in Table 2 above were dissolved in 87 g of purified water respectively to prepare the second solutions. The first solution was added dropwise to the second solutions to prepare compositions 1 to 8 of the present invention in the form of mixed solutions.

Preparation Example 2: Preparation of Cream, a Skin Pharmaceutical Composition for an External Use The cream for the pharmaceutical composition for an external use was prepared by using the composition of the conventional cream formulation as shown in the following Table 3 below, the compound of Formula (1) as a first component, the second component (cellulosic polymer) and the solvent (diethylene glycol monoethyl ether, polyethylene glycol, dimethyl sulfoxide).

The oil phase and the aqueous phase of Table 3 below were prepared by warming the mixture, a solution of the compound of Formula (1) was prepared by dissolving the compound of Formula (1) in a solvent, the thickening agent was pre-dispersed in a solution, and a solution of each cellulosic polymer was prepared by dissolving the cellulosic polymer in water.

Thereafter, the oil phase and water phase were first emulsified at 65° C., and then the cellulosic polymer dissolved in water was added and the mixture was homogenized. Then, the compound composition of formula (1) dissolved in the solvent was added and the thickening agent and additives were added, followed by homogenization and then cooling to 35° C. to prepare a pharmaceutical composition for the skin in a cream formulation.

TABLE 3

| Unit: wt. % | Component | Com. Ex. 1 | Com. Ex. 2 | Com. Ex. 3 | Ex. 1 | Ex. 2 | Ex. 3 | Ex. 4 |
|---|---|---|---|---|---|---|---|---|
| Oily phase | PEG-30 hydrogenated Castor oil | 3 | 3 | 3 | 3 | 3 | 3 | 3 |
| | Medium chain triglyceride | 0 | 0 | 0 | 0 | 0 | 0 | 0 |
| | Cetostearyl alcohol | 0 | 0 | 0 | 0 | 0 | 0 | 0 |
| | Squalane | 3 | 3 | 3 | 3 | 3 | 3 | 3 |
| | Cyclomethicone | 0 | 0 | 0 | 0 | 0 | 0 | 0 |
| Surfactant | Sorbitan stearate | 0.4 | 0.4 | 0.4 | 0.4 | 0.4 | 0.4 | 0.4 |
| | Polysorbate 60 | 0 | 0 | 0 | 0 | 0 | 0 | 0 |
| | Cetearyl glucoside | 1.5 | 1.5 | 1.5 | 1.5 | 1.5 | 1.5 | 1.5 |
| | Mono/diglyceride | 0 | 0 | 0 | 0 | 0 | 0 | 0 |
| Thickening agent | Carbomer | 0.2 | 0.2 | 0.2 | 0.2 | 0.2 | 0.2 | 0.2 |
| Neutralizing agent | KOH | 0.1 | 0.1 | 0.1 | 0.1 | 0.1 | 0.1 | 0.1 |
| First component | Compound of Formula (1) | 0 | 0 | 1 | 1 | 1 | 1 | 1 |
| Aqueous phase | Butylene glycol | 3 | 3 | 3 | 3 | 3 | 3 | 3 |
| | Glycerine | 5 | 5 | 5 | 5 | 5 | 5 | 5 |
| | Propylene glycol | 0 | 0 | 0 | 0 | 0 | 0 | 0 |
| | Purified water | balance | balance | balance | balance | balance | balance | balance |
| Solvent | Polyethylene glycol 300 | 0 | 0 | 0 | 0 | 0 | 0 | 0 |
| | Polyethylene glycol 400 | 10 | 10 | 10 | 10 | 10 | 10 | 10 |
| | Diethylene glycol monoethyl ether | 0 | 0 | 0 | 0 | 0 | 0 | 0 |
| | DMSO | 0 | 0 | 0 | 0 | 0 | 0 | 0 |
| Second component | MC | 0 | 0 | 0 | 2 | 0 | 0 | 0 |
| | HEC | 0 | 0 | 0 | 0 | 2 | 0 | 0 |
| | HPC LF | 0 | 0 | 0 | 0 | 0 | 2 | 0 |
| | Hypromellose, 3 | 0 | 0 | 0 | 0 | 0 | 0 | 2 |
| | Hypromellose, 4.5 | 0 | 0 | 0 | 0 | 0 | 0 | 0 |
| | Hypromellose, 6 | 0 | 2 | 0 | 0 | 0 | 0 | 0 |
| Additive | Preservative, coloring agent, flavoring agent | quantum satis | quantum satis | quantum satis | quantum satis | quantum satis | quantum satis | quantum satis |

| | Unit: wt. % | Component | Ex. 5 | Ex. 6 | Ex. 7 | Ex. 8 | Ex. 9 | Ex. 10 |
|---|---|---|---|---|---|---|---|---|
| | Oily phase | PEG-30 hydrogenated Castor oil | 3 | 3 | 0 | 0 | 0 | 0 |
| | | Medium chain triglyceride | 0 | 0 | 4.5 | 4.5 | 4.5 | 4.5 |
| | | Cetostearyl alcohol | 0 | 0 | 3.5 | 3.5 | 3.5 | 3.5 |
| | | Squalane | 3 | 3 | 0 | 0 | 0 | 0 |
| | | Cyclomethicone | 0 | 0 | 4.5 | 4.5 | 4.5 | 4.5 |

TABLE 3-continued

| | | | | | | | |
|---|---|---|---|---|---|---|---|
| Surfactant | Sorbitan stearate | 0.4 | 0.4 | 0 | 0 | 0 | 0 |
| | Polysorbate 60 | 0 | 0 | 1.5 | 1.5 | 1.5 | 1.5 |
| | Cetearyl glucoside | 1.5 | 1.5 | 0 | 0 | 0 | 0 |
| | Mono/diglyceride | 0 | 0 | 1.5 | 1.5 | 1.5 | 1.5 |
| Thickening agent | Carbomer | 0.2 | 0.2 | 0.25 | 0.25 | 0.25 | 0.25 |
| Neutralizing agent | KOH | 0.1 | 0.1 | 0.1 | 0.1 | 0.1 | 0.1 |
| First component | Compound of Formula (1) | 1 | 1 | 1 | 1 | 1 | 1 |
| Aqueous phase | Butylene glycol | 3 | 3 | 0 | 0 | 0 | 0 |
| | Glycerine | 5 | 5 | 1 | 1 | 1 | 1 |
| | Propylene glycol | 0 | 0 | 5 | 5 | 5 | 5 |
| | Purified water | balance | balance | balance | balance | balance | balance |
| Solvent | Polyethylene glycol 300 | 0 | 0 | 0 | 0 | 10 | 0 |
| | Polyethylene glycol 400 | 10 | 10 | 10 | 0 | 0 | 0 |
| | Diethylene glycol monoethyl ether | 0 | 0 | 0 | 10 | 0 | 0 |
| | DMSO | 0 | 0 | 0 | 0 | 0 | 10 |
| Second component | MC | 0 | 0 | 0 | 0 | 0 | 0 |
| | HEC | 0 | 0 | 0 | 0 | 0 | 0 |
| | HPC LF | 0 | 0 | 0 | 0 | 0 | 0 |
| | Hypromellose, 3 | 0 | 0 | 2.5 | 2.5 | 2.5 | 2.5 |
| | Hypromellose, 4.5 | 2 | 0 | 0 | 0 | 0 | 0 |
| | Hypromellose, 6 | 0 | 2 | 0 | 0 | 0 | 0 |
| Additive | Preservative, coloring agent, flavoring agent | quantum satis | quantum satis | quantum satis | quantum satis | quantum satis | quantum satis |

In addition to the above cream formulations, formulations containing the compound of Formula (1) which inhibit the formation of crystals can also be prepared.

Formulation Example 1: Gel

A gel containing the compound of Formula (1), solvent (PEG 400) and cellulosic polymer (Hypromellose 6) of the present invention was prepared by a conventional manner according to the composition shown in Table 4 below.

TABLE 4

| Component | wt. % |
|---|---|
| Compound of Formula (1) | 1 |
| Solvent (PEG 400) | 10 |
| Cellulosic polymer (Hypromellose 6) | 2 |
| Alpha-ketoglutaric acid | 1.0 |
| Niacinamide | 1.0 |
| Beta-1,3-glucan | 0.1 |
| Ethylenediamine sodium acetate | 0.05 |
| Glycerine | 5.0 |
| Carboxyvinyl polymer | 0.3 |
| Ethanol | 5.0 |
| Triethanolamine | 0.3 |
| Preservative, flavoring agent | 0.1 |
| Purified water | balance |

Formulation Example 2: Ointment

An ointment containing the compound of Formula (1) of the present invention, solvent (PEG 400) and cellulosic polymer (Hypromellose 3) was prepared by a conventional manner according to the composition shown in Table 5 below.

TABLE 5

| Component | wt. % |
|---|---|
| Compound of Formula (1) | 1 |
| Solvent (PEG 400) | 10 |
| Cellulosic polymer (Hypromellose 3) | 2.5 |
| Alpha-ketoglutaric acid | 1.0 |
| Niacinamide | 1.0 |
| Beta-1,3-glucan | 10.0 |
| Beewax | 10.0 |
| Polysorbate | 5.0 |
| PEG 60 hardened castor oil | 2.0 |
| Sorbitan sesquioleate | 0.5 |
| Vaseline | 5.0 |
| Liquid paraffin | 10.0 |
| Squalane | 5.0 |
| Shea butter | 3.0 |
| Caprylic/capric triglyceride | 5.0 |
| Glycerine | 10.0 |
| Propylene glycol | 10.2 |
| Triethanolamine | 0.2 |
| Preservative, flavoring agent | 0.1 |
| Purified water | balance |

Formulation Example 3: Lotion

A lotion containing the compound of Formula (1) of the present invention, solvent (PEG 400) and cellulosic polymer (Hypromellose 6) was prepared by a conventional manner according to the composition shown in Table 6 below.

TABLE 6

| Component | wt. % |
| --- | --- |
| Compound of Formula (1) | 1 |
| Solvent (PEG 400) | 10 |
| Cellulosic polymer (Hypromellose, 6) | 2 |
| Biovaderm (Biova inc.) hydrolyzed egg shell | 10.0 |
| Shea butter | 3.0 |
| Caprylic/capric triglyceride | 5.0 |
| Glycerine | 10.0 |
| Propylene glycol | 10.2 |
| Triethanolamine | 0.2 |
| Preservative, flavoring agent | 0.1 |
| Purified water | balance |

Experimental Example 1: Particle Size and Dispersion Stability of the Composition of Preparation Example 1

The particle size and dispersion stability of the compositions 1 to 8 of Reference Examples of the present invention prepared in the above Preparation Examples were measured.

The particle size was measured by Dynamic Light Scattering using a laser particle size analyzer (Zetasizer Nano ZS, Malvern Instruments, Southborough, UK). Also, the dispersion stability was calculated by measuring the TSI (Turbiscan Stability Index) using a measuring instrument (Turbiscan AGS, Formulacion, tolouse, France) at a temperature of 50° C. for 24 hours every 2 hours. The particle size (unit: nm) and TSI thus measured are listed in Table 7 below.

Turbiscan, an analytical technique for the dispersion stability used in the present invention, is a technique for optically measuring the dispersion of a formulation using multiple light scattering which can analyze all of the phenomena in which the dispersion stability is lowered, that is, particle migration phenomena such as sedimentation and creaming, and particle size variation such as flocculation and coalescence and thus can be used for various stability studies (Talanta, Volume 50, Issue 2, 13 Sep. 1999, Langmuir, 2004, 20, 9007-9013, Med Chem. 2015 June; 11(4): 391-399). Since it means that the larger the particle size, the crystal grows, the dispersion stability of the pharmaceutical composition can be predicted by measuring the TSI and size measured in the present invention, and the crystallization process of the active compound can be deduced therefrom.

TABLE 7

| | Cellulosic polymer | Size(nm) | TSI |
| --- | --- | --- | --- |
| Reference Example 1 | MC | 2593.3 ± 317.1 | 10.2 ± 1.3 |
| Reference Example 2 | HEC | 1941.5 ± 241.6 | 11.2 ± 0.6 |
| Reference Example 3 | HPC LF | 1876.3 ± 238.0 | 24.2 ± 2.2 |
| Reference Example 4 | HPC EF | 9095.0 ± 1049.9 | 40.4 ± 3.5 |
| Reference Example 5 | Hypromellose 3 | 676.6 ± 28.0 | 6.2 ± 0.6 |
| Reference Example 6 | Hypromellose 4.5 | 1435.6 ± 159.5 | 9.7 ± 0.9 |
| Reference Example 7 | Hypromellose 6 | 1724.9 ± 176.6 | 9.9 ± 1.4 |
| Reference Example 8 | Hypromellose 15 | 3229.7 ± 449.7 | 13.7 ± 2.1 |

As can be seen from Table 7, it was confirmed that Reference Examples 5 to 7 of the present invention have crystals having a relatively small particle size, and the average TSI is relatively low, on the order of 6 to 10 on average. From these, it can be expected that the composition of the present invention using hypromellose significantly inhibits the formation of crystals of the compound of Formula (1) which is an active component.

Referring to Table 7 above, it can be seen that the tendency of TSI was not shown in all cellulosic polymers, and there was a difference in terms of the interaction between the compound of Formula (1) and each cellulosic polymer.

Also, it was confirmed that even when the same hypromellose is used, as the viscosity of the hypromellose increases, the crystal size and TSI of the active substance in the composition tend to increase.

Thus, it can be expected that all of the cellulosic polymers of Reference Examples 1 to 8 will exhibit an inhibitory effect on the formation of crystals of the compound of Formula (1) which is an active ingredient of the pharmaceutical composition of the present invention, and especially, hypromellose among cellulosic polymers will significantly inhibit the formation of crystals of the compound of Formula (1).

Experimental Example 2: Confirmation of the Presence or Absence of Crystal Precipitation after 24 Hours Storage of the Composition of Preparation Example 1

The compositions 1 to 8 of Reference Examples of one aspect of the present disclosure prepared in Preparation Example 1 were stored in a chamber of 40° C. for 24 hours, and then the presence or absence of crystal precipitation was observed using an optical microscope and a polarizing filter (Olympus BX50 Microphotographic System, Toyo, Japan), and the results are shown in FIGS. 1A to 10.

When dark brown irregular particles are observed in the optical image and anisotropic particles were observed in the polarized image at the same position and at the same time, it was judged that there is a crystal precipitation.

As can be seen in FIG. 1, it can be confirmed that all of the compositions 1 to 7 of Reference Examples using cellulosic polymers inhibit crystal precipitation. In particular, it can be confirmed that the crystal precipitation is remarkably inhibited in the compositions 5 to 7 of Reference Examples of one aspect of the present disclosure using hypromellose as a cellulosic polymer.

Experimental Example 3: Confirmation of Stability of Composition of Preparation Example 2

The composition of the cream formulation comprising the cellulosic polymer, as prepared in Preparation Example 2, was stored in a constant temperature chamber at 40° C., which is an acceleration condition, for 2 weeks, and then observed by an optical and polarization microscope (magnification of 100), and the results are shown in FIGS. 2A to 2D.

As can be seen from FIGS. 2a to 2d, it is confirmed that Comparative Example 3, which contains the compound of Formula (1) and not the cellulosic polymer, shows crystal precipitation when compared with Comparative Example 1 which does not contain the compound of Formula (1) and which does not contain the cellulosic polymer.

On the contrary, it is confirmed that the compositions 1 to 3 of Examples using cellulosic polymer such as MC, HEC or HPC inhibit crystal precipitation when compared with Comparative Example 2, which does not contain the compound of Formula (1) and which contains the cellulosic polymer.

Also, it can be seen that the compositions of one aspect of the present disclosure (Example compositions 4 to 7) using hypromellose as a cellulosic polymer significantly inhibit crystal precipitation.

Also, it can be seen that the compositions of one aspect of the present disclosure (Examples 7 to 10) containing the same amount of Hypromellose 3 as a cellulosic polymer and containing PEG 300, PEG 400, diethylene glycol monoethyl ether and DMSO as a solvent, respectively, also significantly inhibit crystal precipitation, and particularly, Example 7 using PEG 400 shows the best crystal precipitation inhibition effect.

It was confirmed from continued subsequent observations that the composition of Example 8 of the invention using hypromellose inhibits crystal precipitation for more than 6 months in a constant temperature chamber at a 40° C. and inhibits crystal precipitation for 31 months under long term storage conditions (FIG. 3).

What is claimed is:

1. A pharmaceutical composition for topical use comprising:
a mixed solution of (R)—N-[1-(3,5-difluoro-4-methanesulfonylamino-phenyl)-ethyl]-3-(2-propyl-6-trifluoromethyl-pyridin-3-yl)-acrylamide represented by Formula (1)

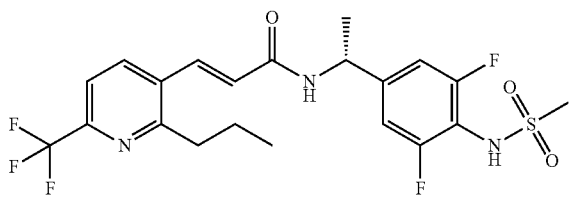 [SMILES: CCCc1nc(C(F)(F)F)ccc1/C=C/C(=O)N[C@H](C)c1cc(F)c(NS(C)(=O)=O)c(F)c1]

dissolved in a solvent; and
an aqueous solution comprising a cellulosic polymer,
wherein the cellulosic polymer is Hypromellose,
wherein the aqueous solution comprising the cellulosic polymer has a viscosity of 2 to 10 mPa·s, a content of 1 to 5 wt. % of the total weight of the composition, and a weight ratio of 1:1 to 3:1 relative to the compound represented by Formula (1).

2. The pharmaceutical composition according to claim 1, wherein the compound of Formula (1) is included in an amount of 0.1 to 1.5 wt. %, 0.5 to 1.2 wt. % or 0.8 to 1.2 wt. % of the total weight of the composition.

3. The pharmaceutical composition according to claim 1, wherein the amount of cellulosic polymer weight present is from 1 to 3 wt. % or 2.5 wt. %.

4. The pharmaceutical composition according to claim 1, wherein the weight ratio of the cellulosic polymer to the compound of Formula (1) is 1.5:1 to 3:1 or 2:1 to 3:1.

5. The pharmaceutical composition according to claim 1, wherein the pharmaceutical composition is formulated into a pharmaceutical composition for an external use which is applied to the skin.

6. The pharmaceutical composition according to claim 1, wherein the pharmaceutical composition is formulated into a cream, gel, patch, aerosol, ointment, plaster, lotion, liniment, or cataplasma formulation.

7. The pharmaceutical composition according to claim 1, wherein the solvent which ensures the solubility of the compound of Formula (1) in the solvent is 100 mg/mL or more.

8. The pharmaceutical composition according to claim 7, wherein the solvent is included in an amount of 5 to 20 wt. %, 5 to 15 wt. % or 8 to 12 wt. % of the total weight of the composition.

9. The pharmaceutical composition according to claim 7, wherein the solvent is selected from the group consisting of diethylene glycol monoethyl ether, polyethylene glycol, 2-pyrrolidone and dimethyl sulfoxide.

10. The pharmaceutical composition according to claim 9, wherein the solvent is diethylene glycol monoethyl ether or polyethylene glycol.

11. The pharmaceutical composition according to claim 10, wherein the solvent is polyethylene glycol 300 or polyethylene glycol 400.

12. A method of inhibiting the formation of crystals in a pharmaceutical composition containing (R)—N-[1-(3,5-difluoro-4-methanesulfonylamino-phenyl)-ethyl]-3-(2-propyl-6-trifluoromethyl-pyridin-3-yl)-acrylamide represented by Formula (1)

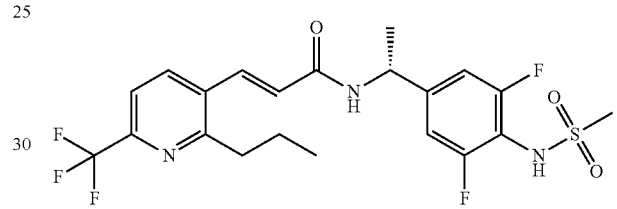

comprising:
dissolving the compound of Formula (1) in a solvent that ensures a solubility of the compound of Formula (1) in the solvent is 100 mg/mL or more to obtain a first solution;
dissolving a cellulosic polymer in water to obtain a second solution;
adding the first solution dropwise to the second solution thereby obtaining a mixed solution,
wherein the cellulosic polymer is hypromellose, and
wherein the cellulosic polymer has a viscosity of 2 to 10 mPa·s, a content of 1 to 5 wt. % of the total weight of the composition, and a weight ratio of 1:1 to 3:1 relative to the compound represented by Formula (1).

13. The method according to claim 12, wherein the solvent is selected from the group consisting of diethylene glycol monoethyl ether, polyethylene glycol, 2-pyrrolidone and dimethyl sulfoxide.

14. The method according to claim 13, wherein the solvent is diethylene glycol monoethyl ether or polyethylene glycol.

15. The method according to claim 13, wherein the solvent is polyethylene glycol 300 or polyethylene glycol 400.

16. The method according to claim 12, wherein the solvent is included in an amount of 5 to 20 wt. %, 5 to 15 wt. % or 8 to 12 wt. % of the total weight of the composition.

* * * * *